(12) United States Patent
Corrie et al.

(10) Patent No.: US 7,737,169 B2
(45) Date of Patent: Jun. 15, 2010

(54) ANIONICALLY SUBSTITUTED 7-NITROINDOLINE DERIVATIVES AND THEIR USES

(75) Inventors: John Corrie, Herts (GB); David Ogden, London (GB); George Papageorgiou, Herts (GB)

(73) Assignee: Medical Research Council, London (GB)

( * ) Notice: Subject to any disclaimer, the term of this patent is extended or adjusted under 35 U.S.C. 154(b) by 400 days.

(21) Appl. No.: 11/507,961

(22) Filed: Aug. 22, 2006

(65) Prior Publication Data

US 2007/0203099 A1 Aug. 30, 2007

Related U.S. Application Data

(60) Provisional application No. 60/711,597, filed on Aug. 26, 2005.

(51) Int. Cl.
*A61K 31/404* (2006.01)
*C07D 209/08* (2006.01)

(52) U.S. Cl. .................................. 514/415; 548/491
(58) Field of Classification Search ............... 548/491
See application file for complete search history.

(56) References Cited

FOREIGN PATENT DOCUMENTS

| WO | WO 00/55133 | 9/2000 |
|----|----|----|
| WO | WO 02/083639 | 10/2002 |
| WO | WO 2004/085394 | 10/2004 |

OTHER PUBLICATIONS

Neurotransmitters [online] (retrieved on Aug. 28, 2008) URL; http://en.wikipedia.org/wiki/Neurotransmitter.*
G. Papageorgiou et al., "Photorelease of Carboxylic Acids frmo 1-Acyl-7-nitroindolines in Aqueous Solution: Rapid and Efficient Photorelease of L-Glutamate", J. Am. Chem. Soc., 121: 6503-6504 (1999).
G. Papageorgiou et al., "Effects of Aromatic Substituents on the Photocleavage of 1-Acyl-7-nitroindolines", Tetrahedron, 56: 8197-8205 (2000).
G. Papageorgiou et al., "Regioselective Nitration of 1-Acyl-4-Methoxyindolines Leads to Efficient Synthesis of a Photolabile L-Glutamate Precursor", Synthetic Communications, 32(10): 1571-1577 (2002).
J. Morrison et al., "Mechanisms of photorelease of carboxylic acids from 1-acyl-7-nitroindolines in solutions of varying water content", Photochem. PHotobiol. Sci., 1: 960-969 (2002).
M. Canepari et al., "Photochemical and pharmacological evaluation of 7-nitroindolinyl-and 4-methoxy-7-nitroindolinyl-amino acids as novel, fast cages neurotransmitters", J. Neurosci. Methods, 112: 29-42 (2001).
M. Canepari et al., "Rapid Report—The conductance underlying the parallel fibre slow EPSP in rat cerebellar Purkinje neurones studies with photolytic release of L-glutamate", J. Physiol., 533: 765-772 (2001).
M. Matsuzaki et al., "Dendritic spine geometry is critical for AMPA receptor expression in hippocampal CA1 pyramidal neurons", Nat. Neurosci., 4: 1086-1092 (2001).
M. Canepari et al., "Evidence for Protein Tyrosine Phosphatase, Tyrosine Kinase, and G-Protein Regulation of the Parallel Fiber Metabotropic Slow WEPSC of Rat Cerebellar Purkinje Neurons", J. Neurosci., 23: 4066-4071 (2003).
G. Lowe, "flash Photolysis Reveals a Diversity of Ionotropic Glutamate Receptors on the Mitral Cell Somatodendritic Membrane", J. Neurophysiol., 90: 1737-1746 (2003).
G. Shepherd et al., "Circuit analysis of Experience-Dependent Plasticity in the Developing Rat Barrel Cortex", Neuron, 38: 277-289 (2003).
M. Smith et al., "Mechanism of the distance-dependent scaling of Schaffer collateral synapses in rat CA1 pyramidal neurons", J. Physiol., 548: 245-258 (2003).
M. Matsuzaki et al., "Structural basis of long-term potentiation in single dendritic spines", Nature, 429: 761-766 (2004).
A. Carter et al., "State-Dependent Calcium Signaling in Dendritic Spines of Striatal Medium Spiny Neurons", Neuron, 44: 483-493 (2004).
I. Bureau et al., "Precise Development of Functional and Anatomical Columns in the Neocortex", Neuron, 42: 789-801 (2004).
M. Canepari et al., "CA2+ Ion Permeability and Single-Channel Properties of the Metabotropic Slow EPSC of Rat Purkinje Neurons", J. Neurosci., 24: 3563-3573 (2004).
Y. Huang et al., "Synthesis and Characterization of 4-Methoxy-7-nitroindolinyl-D-aspartate, a Caged Compound for elective Activation of Glutamate Transporters and N-Methyl-D-aspartate Receptors in Brain Tissue", Biochemistry, 44: 3316-3326 (2005).
W. Maier at al., "Comparative analysis of inhibitory effects of caged ligands for the NMDA receptor", J. Neurosci. Methods, 142: 1-9 (2005).
K. Gee et al., "Synthesis and Photochemistry of a New Photolabile Derivative of GABA. Neurotransmitter Release and Receptor Activation in the Microsecond Time Region", J. Am. Chem. Soc., 116: 8366-8367 (1994)EE.
S. Murov, Handbook of Photochemistry, pp. 3-22, Marcel Dekker, New York (1973).
N. Fertig et al., "Whole Cell Patch Clamp Recording Performed on a Planar Glass Chip", Biophys. J., 82: 3056-3062 (2002) [Abstract].
K. Klemic et al., Biophys. J. "A Simple Technique for Fabricating Planar Patch clamp Electrodes in the Laboratory", Biophys. J., 84: 135a (2003) [Abstract].
S. Friis et al., "Characterization of BK channels on a planar silicon chip", Biophys. J., 84: 295a (2003) [Abstract].

(Continued)

*Primary Examiner*—Rebecca L Anderson
*Assistant Examiner*—Shawquia Young
(74) *Attorney, Agent, or Firm*—Patrick J. Hagan; Dann, Dorfman, Herrell and Skillman, P.C.

(57) ABSTRACT

Anionically substituted 7-nitroindoline derivatives are disclosed and their uses as caged compounds from which effector species such as neurotransmitters and amino acids are releasable on irradiation with light.

9 Claims, 1 Drawing Sheet

OTHER PUBLICATIONS

K. Ng et al., "Glass-based, 96-well plate for automatic parallel patch-clamping", Biophys. J., 84: 296a (2003).

J. Osby, "An Exceptionally Mild Deprotection of Phthalimides", Tetrahedron Letters, 25(20): 2093-2096 (1984).

C. Kaneko et al., "A Photochemical Synthesis of 4-Hydroxyindole", Chemistry Letters, 547-550 (1980).

T. Curtius et al., Ber. Deut. Chem. Ges., 45: 1045-1050 (1912).

E. Prisbe et al., "Synthesis and Antiherpes Virus Activity of Phosphate and Phosphonate Derivatives of 9-[(1,3-dihydroxy-2-propoxy)methyl]guanine", J. Med. Chem., 29: 671-675 (1986).

E. Kalinichenko et al., "3-Deazaadenosine analogues of p5' A2' p5'A2'p5' A: synthesis, stereochemistry, and the roles of adenine ring nitrogen-3 in the interaction with RNase L", Bioorg. Med. Chem., 12: 3637-3647 (2004).

J. Corrie et al., "Caged Nucleotides and Neurotransmitters", Bioorganic Photochemistry: Biological Applications of Photochemical Switches, vol. 2, pp. 244-246, ed. Harry Morrison, Wiley (1993).

J. Costantin et al., "Parallel planar patch-clamp recordings of ion channels using a 384-well substrate", Biophys. J., 84: 295a (2003) [Abstract].

* cited by examiner

ANIONICALLY SUBSTITUTED 7-NITROINDOLINE DERIVATIVES AND THEIR USES

This application claims the benefit of U.S. Provisional Application No. 60/711,597, filed Aug. 26, 2005.

FIELD OF INVENTION

The present invention relates to anionically substituted 7-nitroindoline derivatives and their uses as caged compounds from which effector species such as neurotransmitters and amino acids are releasable on irradiation with light.

BACKGROUND OF INVENTION

The present inventors have previously described the preparation of 7-nitroindoline-caged neuroactive amino acids, particularly the 5-methoxycarbonylmethyl and 4-methoxy compounds 1 and 2 that are able to release L-glutamate on a sub-µs time scale in response to a rapid pulse of near-UV light (typically in the ~300-350 nm range).[1-3] Evaluation of the pharmacology of these reagents showed that the glutamate conjugates 1 and 2 had no evidence of binding to glutamatergic receptors,[4] making them particularly suitable as reagents to investigate synaptic function in neuronal cells and both reagents have become established as experimental tools for this purpose.[5]

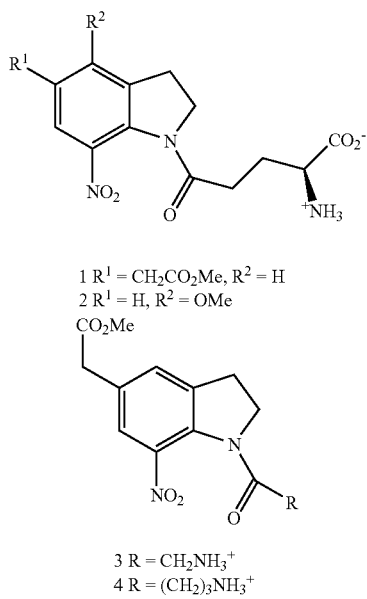

1 $R^1 = CH_2CO_2Me$, $R^2 = H$
2 $R^1 = H$, $R^2 = OMe$

3 $R = CH_2NH_3^+$
4 $R = (CH_2)_3NH_3^+$

The overall photocleavage reaction of these compounds in aqueous solution is shown in Scheme 1.

Scheme 1

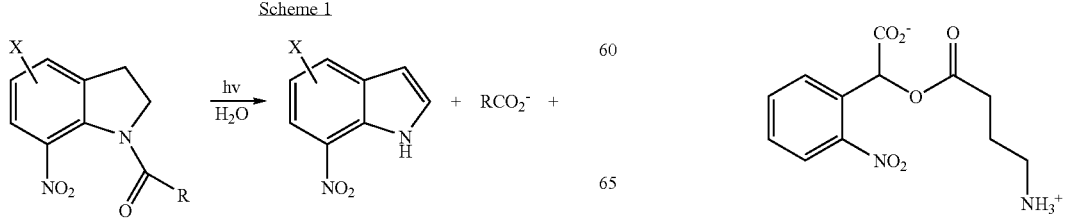

In contrast to these glutamate reagents, conjugates of γ-aminobutyrate (GABA) and glycine corresponding to structure 1, i.e. compounds 3 and 4, were found to show binding to their relevant GABA or glycine receptors on neuronal cells, and the response to photolytic release of GABA or glycine though useful was therefore blunted.[4]

WO 00/55133, WO 02/083639 and WO 2004/085394 describe the present inventors' work in developing novel photoreleasable 7-nitroindoline compounds and improved methods for their synthesis.

However, it remains a challenging problem in the art to provide compounds that cage effectors such as neurotransmitters and amino acids that are capable of reducing or abolishing the interaction of the effector with its receptor. This is a particular problem as the caged compounds also need to be chemically robust enough to be used under the conditions found in biological systems and in experimental electrophysiological research.

SUMMARY OF THE INVENTION

Broadly, the present invention addresses the problem of providing 7-nitroindoline compounds for caging effector species in which the residual binding observed with certain prior art caged 7-nitroindoline conjugates to their receptors is reduced or abolished, and in particular to provide 7-nitroindoline conjugates of GABA and glycine to complement the glutamate derivatives 1 and 2 used in experimental electrophysiological research.

The present inventors designed the compounds described herein starting from the realisation that other workers had reported that the α-carboxy-2-nitrobenzyl ester of GABA (5) had no pharmacological effects,[6] although it is generally recognised that esters of this type are susceptible for hydrolysis and are therefore prone to leak the caged bioeffector prior to photolysis, making them less suitable for electrophysiology than the nitroindoline compounds. The latter are very resistant to hydrolysis at neutral pH.[1] The inventors hypothesised that the negative charge of the α-carboxylate group present in 5 was beneficial in terms of blocking binding of 5 to GABA receptors and therefore set out to prepare a nitroindoline derivative of GABA with a high concentration of negative charge. The target species was the diphosphate 6 and it was anticipated that a successful outcome in terms of a lack of pre-photolysis pharmacology for this GABA compound could be beneficial for other effector species such as a glycine conjugate. The design of 6 incorporated a substituted variant of the 4-methoxy group that is present in 2, since the latter had been shown to have beneficial effects on the efficiency of the photocleavage reaction.[2]

5

-continued

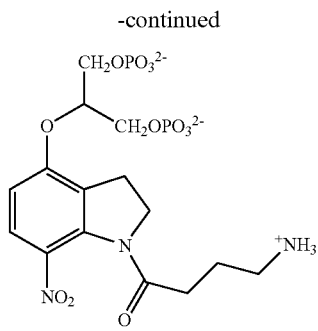

Accordingly, in a first aspect, the present invention provides a compound represented by the formula:

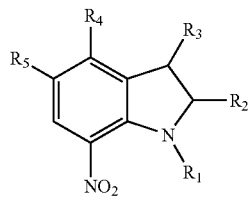

wherein:

$R_1$ is an effector species linked to the nitrogen atom at the 1-position of the indoline ring via an acyl linkage or is a group which is capable of linkage to an effector species;

$R_2$ and $R_3$ are selected from hydrogen, a substituted or unsubstituted alkyl group, or $R_2$ and $R_3$ together form a substituted or unsubstituted cycloalkyl group;

$R_4$ is a group having a strong negative charge; and $R_5$ is hydrogen, a substituted or unsubstituted alkyl group, a substituted or unsubstituted phenyl group, a triplet sensitising group, or a group represented by $(CH_2)_nY$ or $(CH_2)_mO(CH_2)_nY$;

wherein m and n are independently between 1 and 10 and Y is selected from hydrogen, $CO_2H$ or salts thereof, $OPO_3^{2-}$ or salts thereof, $OSO_3^-$ or salts thereof, or $CO_2R_6$, wherein $R_6$ is an alkyl or substituted alkyl group;

or a salt, protected form or partially or fully protonated form of the compound.

Preferred examples of effector groups include neurotransmitters and amino acids such as glycine ($R_1$ is $-CO-CH_2-NH_2$), GABA ($R_1$ is $-CO-CH_2-CH_2-CH_2-NH_2$) and glutamate (e.g. isomers including $R_1$ is $-CO-CH(CH_2CH_2COOH)-NH_2$ or $-CO-CH_2CH_2CH(COOH)-NH_2$). Particularly preferred effector groups are GABA and glycine as they are difficult to cage effectively using some of the previous 7-nitroindoline derivatives.

In relation to the $R_4$ group, by a group having a strong negative charge, we mean a group having at least three and more preferably at least four negative charges provided by its substituents. In a preferred embodiment, the $R_4$ group is a straight chain or branched alkoxy group (e.g. a $C_{1-10}$ alkoxy group) linked to the 7-nitroindoline via the oxygen atom of the alkoxy group. The negative charge may be provided by phosphate, biphosphate, triphosphate or sulphate groups. Where the $R_4$ group has phosphate or sulphate groups, at least two such substituents will be needed to provide the necessary strong negative charge. In all aspects of the present invention, the compounds may be provided as salts or as partly or fully protonated forms of the compounds. By way of example, the $R_4$ group not only includes groups comprising a plurality of $-PO_3^{2-}$ groups, but also partially and fully protonated forms of this substituent such as $-PO_3H^-$ and $PO_3H_2$.

Where a phosphate group or groups provides the strong negative charge, $R_4$ may be substituted with two, three or more monophosphate groups or by a biphosphate or triphosphate group. Preferred examples of phosphate containing $R_4$ groups include:

A $R_4$ group with two monophosphate groups:

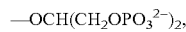

A $R_4$ group with three monophosphate groups:

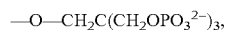

A $R_4$ group with a biphosphate group:

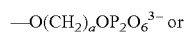

A $R_4$ group with a triphosphate group:

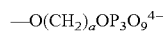

wherein a is an integer between 1 and 5.

The compounds of the present invention may be provided in the form of salts, including for example $Li^+$, $Na^+$, $K^+$, $Rb^+$, $Cs^+$, trialkylammonium or tetraalkylammonium salts of the compound represented by the above formula.

In embodiments of the present invention in which the 1-acyl-7-nitroindolines are used to cage an effector group, preferably the linkage to $R_1$ group is represented by:

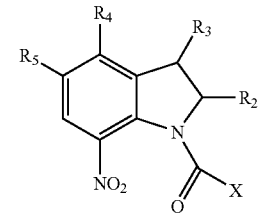

wherein X is $-C-R$, $-O-R$ or $-NH-R$, wherein R is the remaining part of the effector species. Examples of preferred effector species are described below and include glycine ($HOC(O)-CH_2-NH_2$), GABA ($HOC(O)-CH_2-CH_2-CH_2-NH_2$) and glutamate ($HOC(O)-CH(CH_2CH_2COOH)-NH_2$ or $HO-CO-CH_2CH_2CH(COOH)-NH_2$).

In some embodiments, the compounds of the invention may include a triplet sensitizing group at position R5, for example to improve the efficiency of photolysis or introduce into the compound other properties useful in high throughput screening applications and patch clamp experiments. Suitable triplet sensitizing groups are well known to those skilled in the art and are discussed in WO 2004/085394 and Tables 1-1 and 1-2 of *the Handbook of Photochemistry*.[7]

The skilled person is well able to balance these factors and, based on the teaching herein, to select suitable triplet sensitising groups, referring to the documents cited above. Examples of triplet sensitising groups that may be used in the compounds of the invention include unsubstituted and substituted benzophenones, particularly those having one or more substituents at the 4 or 4,4' positions such as substituted or unsubstituted alkyl, alkoxy, dialkyl or dialkoxy groups.

One preferred substituent may be defined as —O—(CH$_2$)$_n$—OPO$_3{}^{2-}$, where n is an integer between 1 and 10, and is preferably where n=2. Compounds of this sort, such as the exemplified 4,4'-dialkoxy derivatives, have strong near-UV absorption. Other types of preferred triplet sensitising groups include, but are not limited to, substituted and unsubstituted anthrones, substituted and unsubstituted xanthones, substituted and unsubstituted carbazoles, substituted and unsubstituted triphenylenes and substituted and unsubstituted heterocyclic analogues of benzophenone such as 3- or 4-benzoylpyridines. The triplet sensitising group(s) may be linked directly to the 4 and/or 5-position of the nitroindoline ring, or via a linker group, which itself can link to the triplet sensitising group directly or via one of its substituents, if present.

Accordingly, the strongly anionic grouping of the present invention provides a class of 7-nitroindoline caged effectors that have reduced binding of the effectors to their receptors in caged form that makes these compounds particularly apt for use in high throughput screening applications and patch clamp experiments.

In a further aspect, the present invention provides a method employing a 7-nitroindoline as defined herein that is coupled at the nitrogen atom of the heterocyclic atom to an effector species by an amide bond, the method comprising irradiating the effector species/7-nitroindoline conjugate with near-ultraviolet light to cause it to photolyse and release the effector species. Examples of such methods are disclosed below and include patch clamp experiments and high throughput screening methods.

Embodiments of the present invention will now be described in more detail by way of example and not limitation with reference to the accompanying FIGURE.

DETAILED DESCRIPTION

Substituents

Figure 1:
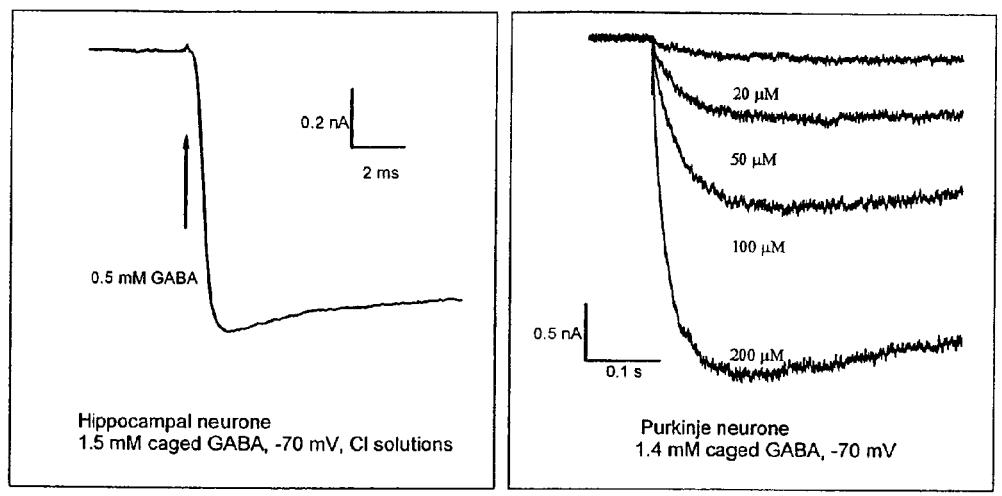
FIG. 1. Current responses to photolytic release of GABA from various concentrations of 6 onto two different neuronal cells, as specified in the FIGURE. The experimental set-up and protocol was as described in reference 4.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known in the art, and methods for their formation and introduction into a variety of parent groups are also well known.

Alkyl: The term "alkyl," as used herein, pertains to a monovalent moiety obtained by removing a hydrogen atom from a carbon atom of a hydrocarbon compound having from 1 to 20 carbon atoms, or more preferably 1 to 10 carbon atoms, which may be aliphatic or alicyclic, and which may be saturated, partially unsaturated, or fully unsaturated. Thus, the term "alkyl" includes the sub-classes alkenyl, alkynyl, cycloalkyl, etc., discussed below.

Alkoxy: preferably alkoxy groups are represented by O(CH$_2$)$_n$—Y, where n and Y are defined above, and may be optionally substituted with one or more of the groups below.

In embodiments of the invention in which a substituted phenyl groups is present, it may include one or more of the substituents set out below. If the phenyl group has less than the full complement of substituents, they may be arranged in any combination. For example, if the phenyl group has a single substituent other than hydrogen, it may be in the 2-, 3-, or 4-position. Similarly, if the phenyl group has two substituents other than hydrogen, they may be in the 2,3-, 2,4-, 2,5-, 2,6-, 3,4-, or 3,5-positions. If the phenyl group has three substituents other than hydrogen, they may be in, for example, the 2,3,4-, 2,3,5-, 2,3,6-, 2,4,5-, 2,5,6-, or 3,4,5-positions. If the phenyl group has four substituents other than hydrogen, they may be in, for example, the 3,4,5,6-, 2,4,5,6-, 2,3,5,6-, 2,3,4,6-, or 2,3,4,5-positions.

In preferred embodiments of the present invention the substituted functional groups as defined herein may be independently selected from: halo; hydroxy; ether (e.g., C$_{1-7}$alkoxy); formyl; acyl (e.g., C$_{1-7}$alkylacyl, C$_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., C$_{1-7}$alkylthio); sulfonic acid; sulfonate; sulfone; sulfonyloxy; sulfinyloxy; sulfamino; sulfonamino; sulfinamino; sulfamyl; sulfonamido; phosphoryl groups such as phosphate —O—P(O)(OH)$_2$; thiophosphate —O—P(S)(OH)$_2$; phosphate esters —O—P(O)(OR')$_2$; thiophosphate esters —O—P(S)(OR')$_2$; phosphonate —O—P(O)OHR'; thiophosphonate —O—P(S)OHR'; substituted phosphonate —O—P(O)OR'$_1$R'$_2$; substituted thiophosphonate —O—P(S)OR'$_1$, R'$_2$; —O—P(S)(OH)(SH); cyclic phosphate, wherein R', R', and R'$_2$ are independently hydrogen or C$_{1-10}$ unsubstituted or substituted alkyl or aryl; C$_{1-7}$alkyl (including, e.g., unsubstituted C$_{1-7}$alkyl, C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl); C$_{3-20}$heterocyclyl; or C$_{5-20}$aryl (including, e.g., C$_{5-20}$carboaryl, C$_{5-20}$heteroaryl, C$_{1-7}$alkyl-O$_{5-20}$aryl and C$_{5-20}$haloaryl)).

In one preferred embodiment, the substituent(s), often referred to herein as R, are independently selected from:

—F, —Cl, —Br, and —I;

—OH;

—OMe, —OEt, —O(tBu), and —OCH$_2$Ph;

—SH;

—SMe, —SEt, —S(tBu), and —SCH$_2$Ph;

—O—P(O) (OH)$_2$, —O—P(S)(OH)$_2$, —O—P(O)(OR')$_2$, —O—P(S)(OR')$_2$, —O—P(O)OHR', —O—P(S)OHR', —O—P(O)OR'$_1$R'$_2$, —O—P(S)OR'$_1$R'$_2$, —O—P(S)(OH)(SH) and cyclic phosphate, R', R'$_1$ and R'$_2$ defined as above;

—C(=O)H;

—C(=O)Me, —C(=O)Et, —C(=O)(tBu), and —C(=O)Ph;

—C(=O)OH;

—C(=O)OMe, —C(=O)OEt, and —C(=O)O(tBu);

—C(=O)NH$_2$, —C(=O)NHMe, —C(=O)NMe$_2$, and —C(=O)NHEt;

—NHC(=O)Me, —NHC(=O)Et, —NHC(=O)Ph, succinimidyl, and maleimidyl;

—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;

—CN;

—NO$_2$;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, and —CH$_2$CF$_3$;

—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;

—CH$_2$OH, —CH$_2$CH$_2$OH, and —CH(OH)CH$_2$OH;

—CH$_2$NH$_2$, —CH$_2$CH$_2$NH$_2$, and —CH$_2$CH$_2$NMe$_2$; and, optionally substituted phenyl.

Unless otherwise specified, included in the above definition of substituents are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Similarly, a reference to the strongly negatively charged group R$_4$ includes the anionic form of the compound, a partially or fully protonated form of the compound, and also a salt or solvate thereof or a conventional protected forms. By way of example, compounds with two monophosphate groups (e.g. —O—CH$_2$CH(OPO$_3^{2-}$)CH$_2$OPO$_3^{2-}$ or —OCH(CH$_2$OPO$_3^{2-}$)$_2$), three monophosphate groups (e.g. —O—CH$_2$ (CHOPO$_3^{2-}$)$_2$CH$_2$OPO$_3^{2-}$ or —O—CH$_2$C(CH$_2$OPO$_3^{2-}$)$_3$, a biphosphate group (e.g. —O(CH$_2$)$_a$OP$_2$O$_6^{3-}$) or a triphosphate group (e.g. —O(CH$_2$)$_a$OP$_3$O$_9^{4-}$), wherein a is an integer between 1 and 5, may all be provided in the form of such salts, solvates and protonated or protected forms. By way of example, phosphate groups may be present in their anionic form —PO$_3^{2-}$ and also as —PO$_3$H$^-$ and —PO$_3$H$_2$ groups. Such species, and their permutations in a bis- or tris-monophosphate or in bi- or tri-phosphates may be present depending on the ambient pH of solutions containing the compound of the invention.

Effector Species

The R$_1$ group can be an effector species or a group capable of being coupled to or converted into an effector species. The effector species is preferably linked to the indoline via an acyl linkage, which may be derived either from a carboxylate moiety inherently present in the effector or as part of a carbamate or urea linkage between the effector and the indoline, for example:

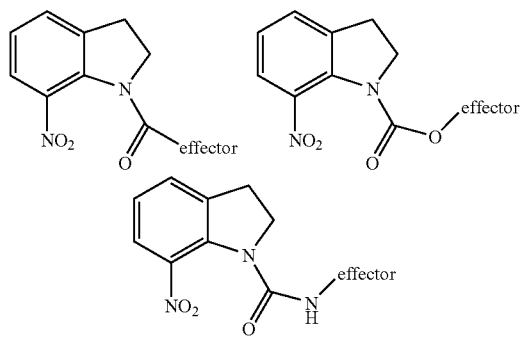

Depending on particular cases, the linkage to a hydroxyl or amino group on the effector may be performed either before or after the nitration reaction according to the present invention. Where the linkage of effector to indoline is carried out post nitration, it can be accomplished as follows:

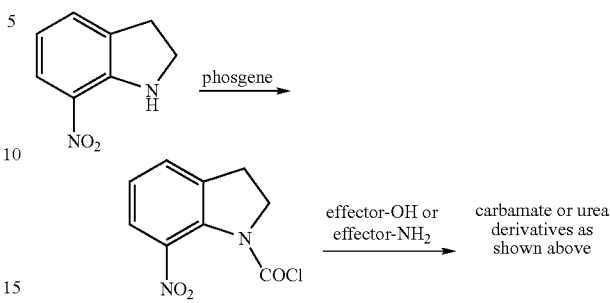

In cases where the effector species is resistant to the nitration conditions, the non-nitrated indoline can be taken through the same steps to create the acyl linkage to the effector species.

Examples of effector species include labels, drugs, toxins, or carrier or transport molecules. Effector species preferably have a carboxylic acid group which can be coupled to the nitrogen atom at the 1-position on the indoline to form an acyl linked effector species.

Techniques for coupling the photocleavable group to both peptidyl and non-peptidyl coupling partners are well known in the art. In preferred embodiments, the effector species is a biologically active compound such as an amino acid (either L or D-amino acids), and more particularly neuroactive amino acids such as L-glutamate, GABA and glycine. The procedures described herein can also be readily adapted to linking larger effector groups such as oligopeptides or polypeptides to the photocleavable group. Examples of especially suitable peptides are as follows: thyrotrophin releasing hormone TRH; enkephalins (locally acting endogenous opiates); bradykinin; and angiotensin II. Generally, the methods described herein are applicable to any oligopeptides with non-amidated C-termini.

The synthesis of photoreleasable compounds including oligo or polypeptide effector species can be achieved by linking a terminal amino acid (i.e. the C-terminal amino acid) to the photocleavable group and then using polypeptide chain extension techniques to build up the peptide chain stepwise, or by coupling an oligopeptide or polypeptide to the terminal amino acid linked to the photocleavable group. Standard peptide synthesis techniques could also be adapted by linking to the synthesis resin a suitably substituted alkoxy group at position 4. This would give a resin containing the protecting group and C-terminal residue which could be elaborated and eventually cleaved from the resin by standard techniques.

If the photoreleasable compound is synthesized using the scheme described in the examples below with the effector species introduced prior to the nitration reaction, it is preferred that the effector species is stable to the nitration reaction carried out after it is attached to the nitrogen of the indoline ring. In the case of amino acids, this means that the use of amino acids other than tryptophan, tyrosine, cysteine or methionine is preferred.

In other aspects, the present invention provides precursor compounds in which the effector species has not been linked to the photocleavable group (e.g. X is H, COY as defined above, or COCl) and/or in which the nitration reaction has not been carried out (e.g. the substituent at the 7-position is hydrogen).

After administration, the photoreleasable compound can be activated to release the effector species, conveniently by exposure to a flash of UV light.

Preferred applications of the compounds of the invention are in patch clamp experiments and/or in high throughput screening (HTS). Patch clamp experiments are a widely used technique in biology that was originally developed to observe ionic current produced when ions flow through ion channels, membrane proteins that regulate the flow of ions across cellular membranes and hence the physiology of cells. This ionic movement creates an electrical current which is tightly regulated by specific signals that cause the ion channels to open and close. The movement of the ions leads to a measurable electrical current that forms the basis of processes such interneuronal and neuromuscular communication. For an introductory review of the technique, see for example Patch Clamping: An Introductory Guide, Molleman, Wiley Europe, 2002.

From its origin, the technique has found many applications including the observation of the function of proteins in lipid bilayers, monitoring the synaptic transmission between neurones in the brain and monitoring changes that occur in cell membranes during secretion. In basic terms, patch clamp experiments employ a pipette or capillary having an opening between about 0.1 and 5 μm. A portion of the cell wall of a single cell is sucked into the opening allowing potentials to be applied to and measured across the cell membrane. More recently, patch clamping has been used in assays for the effect of drugs on cells particularly those used to affect ion channels such as sodium or potassium channels.

As the caged compounds of the present invention are compatible with the biological conditions used in such cell based assays and are capable of releasing effector species on irradiation, they are particularly suited in cell based assays such as patch clamp experiments and high throughput screening methods. Thus, the compounds of the invention can be introduced into the vicinity of a cell, e.g. in a patch clamp experiment, and a concentration of the active effector species generated in very short period on irradiation. This enables the effect of the released species to be studies under controlled circumstances.

Several reports indicate progress towards high throughput screening in association with patch clamping[8], and neuroactive amino acids and their interactions with specific receptors are targets for therapeutic intervention. The ability to apply a sub-millisecond pulse of neuroactive amino acid to patch clamped cells within a multiple assay format is likely to be an important component of successful assays, avoiding the well-known desensitisation of receptors on neuronal cells that occurs in the prolonged presence of the neuroactive amino acid. In one possible embodiment of such an assay, the array of patch clamped cells would be set up with specific test compounds together with the caged native neuroactive amino acid (such as L-glutamate, GABA or glycine) and the native compound would then be photoreleased by brief illumination of the array.

Experimental

As described in the above Summary of the Invention, a preferred compound has the structure 6. Synthesis of 6 began from the indol-4-oxymalonate ester 8, that was itself synthesised as shown in Scheme 2. Direct alkylation of 4-hydroxyindole with diethyl bromomalonate gave a mixture of products 7 and 8. The formation of the anomalous product 7 could be suppressed by prior acyl protection of the indole. This was realised sequentially by formation of the TBDMS ether 9, acylation of the nitrogen with benzyl chloroformate to give 10 and removal of the TBDMS ether. The phenol 11 could then be cleanly alkylated by diethyl bromomalonate to give a single product 12, and hydrogenolysis gave the required compound 8 in good yield (overall 40% from 4-hydroxyindole).

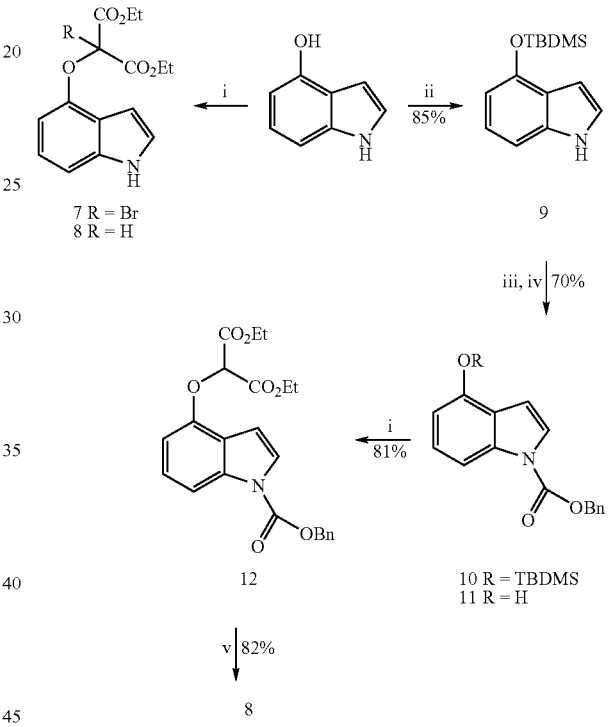

Reagents and conditions: (i) diethyl bromomalonate, $K_2CO_3$, acetone; (ii) TBDMS-Cl, imidazole, $CH_2Cl_2$; (iii) Cbz—Cl, $Bu_4NBr$, powdered NaOH, $CH_2Cl_2$; (iv) TBAF, HOAc, THF; (v) $H_2$, Pd—C, EtOH.

The synthesis was then carried forward (Scheme 3) by reduction of the two ester groups and protection of the resulting diol 13 as its bis-TBDMS ether 14. In fact, at this point, various combinations of protecting groups were explored, including the diacetate of the diol 13 and BOC or phthalimide protection of the GABA moiety that was to be introduced in the next stage. For various reasons, the only successful route was that described below, using the TBDMS-protected compound 14 and a phthalimide-protected GABA. Thus 14 was reduced with sodium cyanoborohydride-acetic acid and the crude product was coupled with 4-phthalimidobutyric acid. The resulting product was found to be a mixture of four compounds 15-18, that were separated and identified by a combination of elemental analysis, $^1H$ NMR spectrometry and mass spectrometry.

Scheme 3.

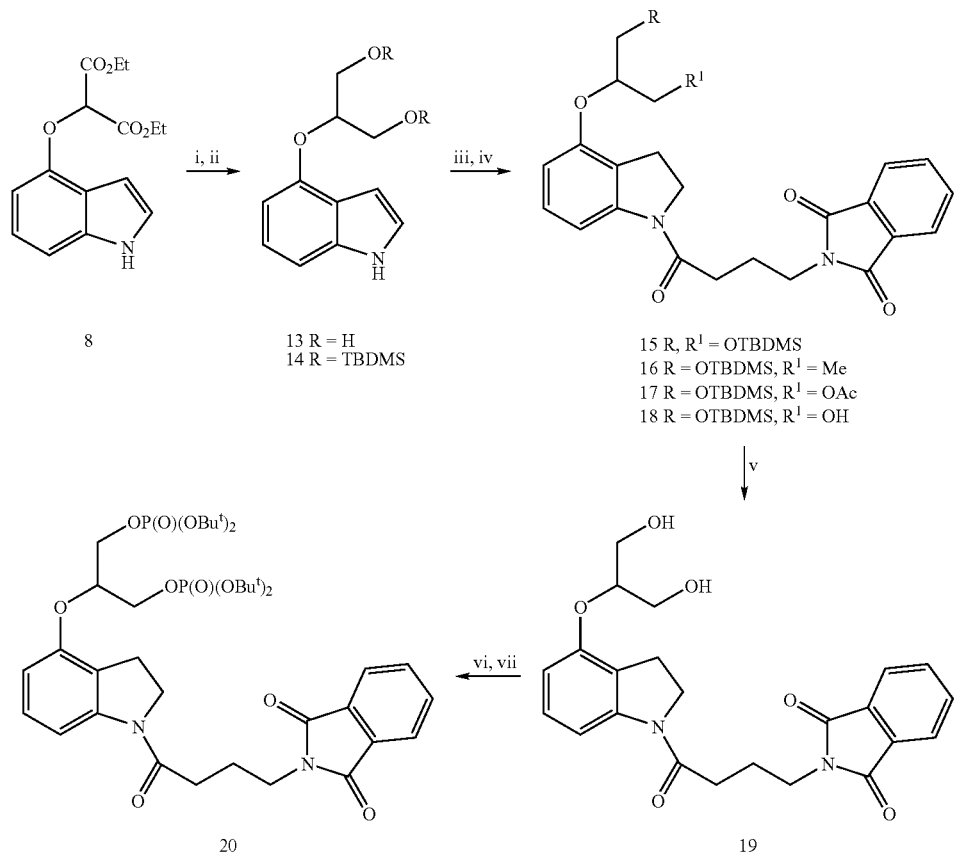

Reagents and conditions: (i) LiAlH$_4$, Et$_2$O; (ii) TBDMS-Cl, imidazole, CH$_2$Cl$_2$; (iii) NaBH$_3$CN, AcOH; (iv) 4-phthalimidobutyric acid, EDC; (v) TBAF, THF; (vi) Et$_2$NP(OBu$^t$)$_2$, 1H-tetrazole, THF; (vii) MCPBA, CH$_2$Cl$_2$.

The mixture of these four compounds could not be fully separated, and it was more convenient to treat the crude mixture with tetrabutylammonium fluoride, which converted the main components 15 and 18 to the diol 19.

Chromatographic separation of the latter, crystalline compound from the desilylated mono-alcohol by-products derived from 16 and 17 was readily achieved to give 19 in 57% overall yield from the indole 14. Conversion to the protected phosphate 20 was then achieved by conventional means.

Although the synthesis up to this point had been relatively straightforward, with appropriate characterisation of intermediates at each stage, its completion to give the desired compound 6 was carried forward without full characterisation until the final product. This was largely because of difficulties encountered with the integrity of the protecting groups and a need to get to the final product 6 for pharmacological evaluation. Thus, the protected phosphate 20 was subjected to nitration under homogenous conditions with cupric nitrate-acetic anhydride. We have previously used the claycop reagent for nitration during preparation of 2 to obtain good regioselectivity in favour of the 7-nitro isomer.[9] However, from the present and other work, we have found that the presence of a bulky substituent on the 4-oxy group inhibited this heterogeneous nitration, presumably because the nitroindoline substrate cannot enter the clay lattice of claycop. Thus it was necessary to use mild, homogeneous nitration. In fact, with substrate 20 the regioselectivity of homogeneous nitration in favour of the 7-nitro isomer was remarkably good, apparently giving only 10-15% of the unwanted, 5-nitro isomer. Nevertheless, the reaction mixture was quite complex and attempted chromatography on silica gel resulted in the loss of much material. It seemed likely that the phosphate groups had been partially deprotected under the reaction conditions, resulting in a charged species and it was decided instead deliberately to remove the phosphate protecting groups, thereby giving a water-soluble species. Thus the crude reaction mixture from the nitration was treated with TFA, and the resulting water-soluble mixture was analysed by reverse-phase HPLC. In addition to some small, fast-eluting peaks, there was one major peak, followed by a second, much less intense peak. From a combination of UV-visible spectroscopy and previous, pilot experiments not discussed here, it appeared likely that these were respectively the 7- and 5-nitro isomers 21 and 22 respectively, in which the phthalimide protecting group was still present. Preparative reverse-phase HPLC resolved these two species and the major isomer, after conversion to its tetrakis(tetrabutylammonium) salt to improve its solubility in a predominantly organic solvent, was treated with sodium borohydride in isopropanol-water (4:1), followed by heating in dilute aqueous acetic acid to remove the phthalimide protecting group. The procedure was based on a previous report of these conditions for phthalimide removal.[10] Analytical reverse-phase chromatography showed a major and a minor peak. UV-visible spectroscopy of each component was compatible with formulation of the major peak as the required final product 6, while the more highly retained, minor peak appeared to have undergone cleavage of the amide bond to give the deacylated indoline 23.

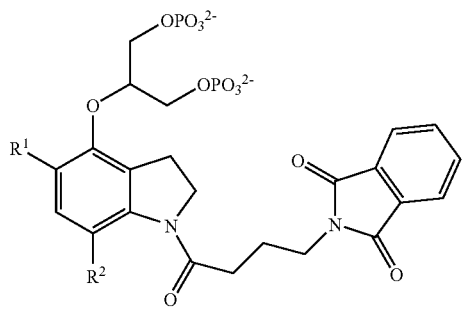

21 R[1] = H, R[2] = NO$_2$
22 R[1] = NO$_2$, R[2] = H

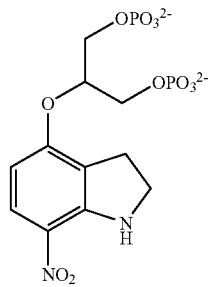

23

The compounds were too strongly hydrophilic to permit separation by preparative reverse-phase HPLC, but preparative anion-exchange chromatography readily resolved the two species. The desired compound 6 was recovered from the eluate by precipitation as a barium salt and finally resolubilised as its sodium salt with a cation exchange resin.

Improved synthesis of (6)

Although the synthesis described above was capable of producing the target compound 6, the methods were somewhat cumbersome and the overall yield might be improved upon. In view of the promising pharmacological data, we sought a more effective synthesis. The two major difficulties of the original route were (i) complications during reduction of the indole 14, which resulted in the mixture of products 15-18 as described above, and (ii) maintaining the integrity of the phthalimido protecting group during the synthesis and removing it at the end. To avoid these problems, we changed to a route in which acetate protecting groups were used for the 1,3-dihydroxypropyl side chain instead of silyl groups as described above, and the nitrogen atom of the eventual GABA side chain was carried through the synthesis as an azido group until the final stages.

To this end, the indolyloxymalonate 8 was reduced as before (Scheme 3) and the diol 13 was acetylated to give 24 (Scheme 4). Reduction with sodium cyanoborohydride-acetic acid, followed by coupling with 4-azidobutyric acid,[12] gave the crystalline azide 25 that was nitrated under homogeneous conditions (copper(II) nitrate-CH$_2$Cl$_2$-acetic anhdride). The heterogeneous nitration conditions previously used for related 1-acyl-4-methoxyindolines[2b] were unsuccessful with 25, evidently because the large 4-alkoxy substituent prevented the molecule from entering the lattice structure of the claycop reagent. Nevertheless, the regiochemistry of the homogeneous nitration in this case was remarkably favourable and gave a mixture of the desired 7-nitro compound 26 and its 5-nitro isomer in a ratio of ~5:1. The pure 7-nitro isomer 26 could be isolated in ~70% yield and hydrolysed by mild alkali to the crystalline diol 27.

Diol 27 was poorly soluble in solvents such as acetonitrile or tetrahydrofuran, and phosphorylation by phosphoramidite chemistry, for example as described herein for synthesis of 20, was consistently unreliable. We turned instead to phosphorylation with phosphorus(V) reagents, of which pyrophosphoryl chloride has successfully been used for direct preparation of phosphate monoesters from a range of substrates, including diols of similar substructure to the 2-alkoxypropane-1,3-diol subunit present in 27.[13] Treatment of a suspension of 27 in anhydrous ethyl acetate with excess pyrophosphoryl chloride smoothly gave the diphosphate 28 after aqueous quench. The aqueous solution contained substantial quantities of inorganic salts that made subsequent reactions difficult, so the material was desalted by reverse-phase HPLC. This was successful only by using mobile phases based on triethylammonium salts, where ion-pairing with the lipophilic cation enabled the highly polar diphosphate 28 to be retained on the column. Subsequent reduction of the azido function with triphenylphosphine in mildly acidic solution gave initially the iminophosphorane 29, which was hydrolysed to the required amine product 6 in dilute HCl (pH 1) at room temperature. The more usual hydrolysis of iminophosphoranes in basic conditions would not have been appropriate because of the susceptibility to cleavage of the 1-acyl group, assisted by its 4-amino substituent. Finally 6 was purified by anion-exchange chromatography and isolated by precipitation as its Ba$^{2+}$ salt as described above for the previous preparation of the compound. The overall yield (as the sodium salt after exchange from the barium salt) was in the range 30-40% from the diol 27.

Scheme 4

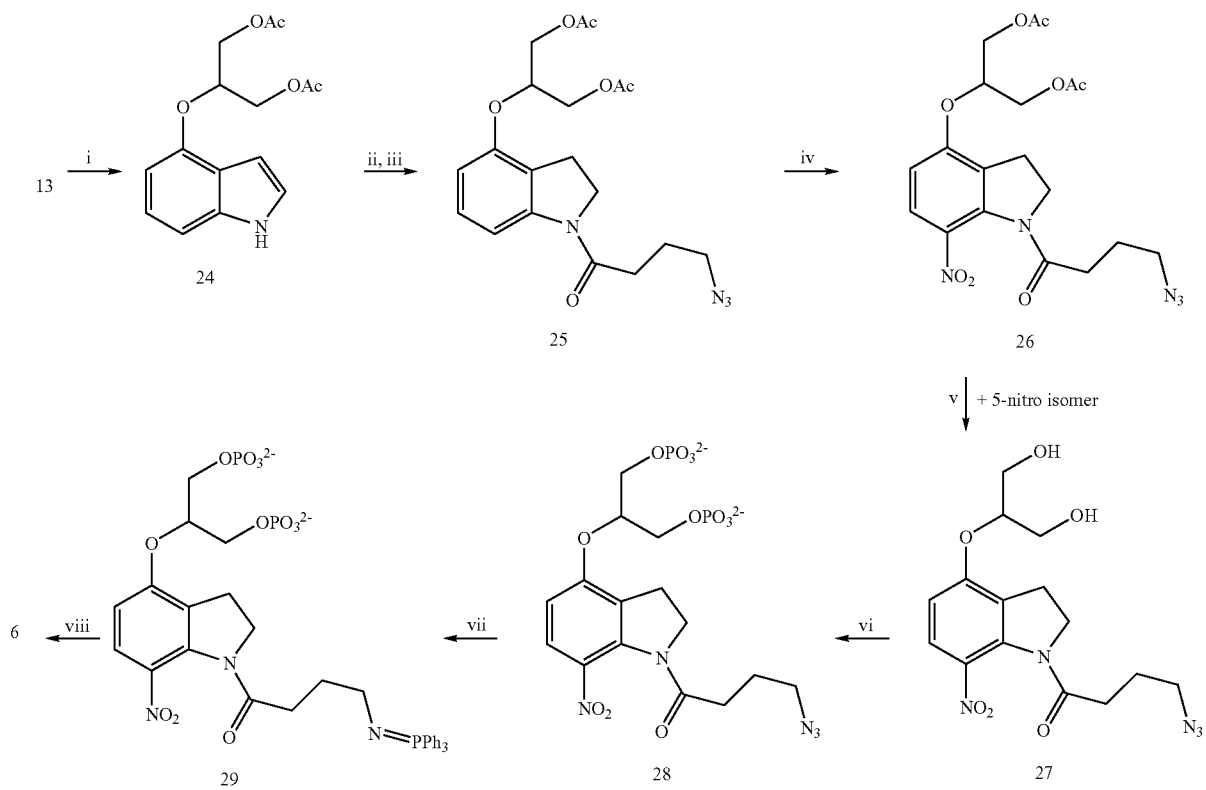

Reagents and conditions: (i) Ac₂O, pyridine;
(ii) NaBH3CN, AcOH; (iii) 4-azidobityric acid, EDC, MeCN;
(iv) Cu(NO3)2, Ac₂O, CH₂Cl₂; (v) NaOH, aq. MeOH; (vi)
pyrophosphoryl chlorife, EtOAc; (vii) Ph₃P, H₂O, DMF;
(viii) 1 M HCl, room temperature.

Pharmacological Assessment of the GABA Cage and the Photorelease of GABA in Neural Tissue A previous evaluation of nitroindoline-caged amino acids in neural tissue has been published[4]. Relevant findings reported there were as follows:—(1) the nitroindoline photolysis reaction itself has no adverse effects on transmission of excitation from presynaptic to postsynaptic neurone; (2) the NI- and MNI-caged glutamate reagents 1 and 2 have no action themselves on glutamate or GABA receptors; (3) the NI-caged GABA 4 interferes with GABA activation of the $GABA_A$ channel isoform. Tests described here were to assess the photolytic efficiency of GABA release in a neurophysiological experiment with particular attention to point (3), namely the presence or absence of interference of the new caged GABA with GABA-activated channels. If interference is low the expectation is that the rise-time of the receptor activation by photoreleased GABA in the presence of high cage concentration should be similar to that generated by endogenously released GABA, rising in 1-2 ms. Data shown in FIG. 1 are the currents through GABA channels (negative polarity) activated with high concentration (left panel: 0.5 mM GABA released, 1.5 mM caged GABA present) showing a fast 1 ms rise-time, and (right panel) four different GABA concentrations (20-200 μm GABA released, 1.4 mM caged GABA present) generated by different photolysis intensities, producing increasing amplitudes and rates of rise at high concentration.

Experimental Details

General Details. $^1$H NMR spectra were determined on JEOL FX90Q or Varian Unityplus 500 spectrometers in deuteriochloroform solution with TMS as internal reference, unless otherwise specified. Merck type 9385 silica gel was used for flash chromatography. Analytical reverse-phase HPLC was performed on a Merck Lichrospher 250×4 mm RP8 column and anion-exchange HPLC was on a Whatman Partisphere 4.6×125 mm SAX column. Mobile phases were as specified in the text and all flow rates were 1.5 mL min$^{-1}$. Preparative reverse-phase HPLC was on a 2×30 cm column (Waters $C_n$ packing material, Cat. No. 20594), with flow rates at 2 mL min$^{-1}$. 4-Hydroxyindole was purchased from Biosynth AG, Staad, Switzerland. Other reagents were from Sigma-Aldrich, Poole, U.K.

Reactions of 4-Hydroxyindole with Diethyl Bromomalonate.

(i) A solution of 4-hydroxyindole (266 mg, 2 mmol) in acetone (20 mL) was cooled to 0° C. under nitrogen and anhydrous potassium carbonate (414 mg, 3 mmol) was added. A solution of commercial diethyl bromomalonate (92%; 624 mg, 2.4 mmol) in acetone (20 mL) was added dropwise over 1 h and the mixture was stirred at 0-5° C. for 1 h, then at room temperature for further 5 h. The very dark solution was filtered, the solid was washed with acetone and the combined filtrates were evaporated. The residue was dissolved in diethyl ether (50 mL), washed with 0.5 M aq. sodium hydroxide and brine, dried and evaporated to a brown viscous oil (535 mg). Flash chromatography (dichloromethane) gave two products. The less polar material was diethyl 2-bromo-2-(indol-4-yloxy)malonate 7 as white crystals (92 mg, 11%), mp 92-93° C. (from diethyl ether-hexanes); $^1$H NMR (500 MHz) δ 8.24 (br s, 1H), 7.19 (d, J=8.1 Hz, 1H), 7.17 (t, J=2.7 Hz, 1H), 7.07 (t, J=8.1 Hz, 1H), 6.94 (d, J=8.1 Hz, 1H), 6.73-6.75 (m, 1H), 4.28-4.38 (m, 4H), 1.23 (t, J=7.1 Hz, 6H). Anal. Calcd. for $C_{15}H_{16}BrNO_5$: C, 48.76; H, 4.36; N, 3.79. Found: C, 48.79; H, 4.43; N, 3.61.

The more polar compound was diethyl 2-(indol-4-yloxy)malonate 8 as white crystals (260 mg, 45%), mp 52-53° C. (from diethyl ether-hexanes); $^1$H NMR (500 MHz) δ 8.25 (br s, 1H), 7.13 (dd, J=3.1, 2.6 Hz, 1H), 7.09 (d, J=7.8 Hz, 1H), 7.05 (t, J=7.8 Hz, 1H, 6.76-6.77 (m, 1H), 6.50 (d, J=7.5 Hz, 1H), 5.35 (s, 1H), 4.28-4.37 (m, 4H), 1.30 (t, J=7.1 Hz, 6H). Anal. Calcd. for $C_{15}H_{17}NO_5$: C, 61.85; H, 5.88; N, 4.81. Found: C, 61.91; H, 6.17; N, 4.68.

(ii) A solution of 4-hydroxyindole (266 mg, 2 mmol) in acetone (20 mL) was cooled to 0° C. under nitrogen and anhydrous potassium carbonate (414 mg, 3 mmol) was added. A solution of commercial diethyl bromomalonate (92%; 520 mg, 2 mmol) in acetone (20 mL) was added dropwise. After stirring for 5 h at room temperature, more diethyl bromomalonate (92%; 520 mg) was added and the mixture was stirred at room temperature overnight. Work up and flash chromatography as above afforded 7 (360 mg, 45%) and 8 (123 mg, 21%).

(iii) A solution of 4-hydroxyindole (266 mg, 2 mmol) in acetone (20 mL) was cooled to 0° C. under nitrogen and anhydrous potassium carbonate (414 mg, 3 mmol) was added. A solution of freshly distilled pure diethyl bromomalonate (574 mg, 2.4 mmol) in acetone (20 mL) was added dropwise and the mixture was stirred at room temperature overnight. Work up and flash chromatography as above afforded 7 (101 mg, 13%) and 8 (199 mg, 34%).

4-(t-Butyldimethylsilyloxy)indole (9). A solution of 4-hydroxyindole (13.31 g, 75 mmol) in dry dichloromethane (400 mL) was treated with imidazole (8.17 g, 120 mmol) and t-butyldimethylsilyl chloride (18.09 g, 120 mmol) and the mixture was stirred at room temperature under nitrogen overnight. The precipitated white solid was filtered off and washed with dichloromethane and the combined filtrates were washed successively with 0.5 M aq. hydrochloric acid, 0.5 M aq. sodium hydroxide and brine, dried and evaporated to give 9 as white crystals (21.03 g, 85%), mp 80-81° C. (from hexanes); $^1$H NMR (500 MHz) δ 8.06 (br s, 1H), 7.08 (dd, J=3.1, 2.4 Hz, 1H), 6.99-7.05 (m, 2H), 6.58-6.59 (m, 1H), 6.52 (dd, J=7, 1.5 Hz, 1H, 1.06 (s, 9H), 0.23 (s, 6H). Anal. Calcd. for $C_{14}H_{21}NOSi$: C, 67.97; H, 8.56; N, 5.66. Found: C, 67.60; H, 8.80; N, 5.57.

Benzyl 4-(t-butyldimethylsilyloxy)indole-1-carboxylate (10). A stirred, ice-cold mixture of 9 (18.56 g, 75 mmol), tetrabutylammonium bromide (2.42 g, 7.5 mmol) and powdered sodium hydroxide (4.0 g, 75 mmol) in dichloromethane (375 mL) was treated dropwise with benzyl chloroformate (95% purity; 20.20 g, 112.5 mmol). The reaction mixture was stirred at room temperature and the progress of the reaction was followed by TLC [ethyl acetate-hexanes (1:9)]. Further aliquots of benzyl chloroformate (each 20.20 g) were added after 1 h and 2 h, and the mixture was stirred at room temperature for a total of 18 h, diluted with water and extracted with dichloromethane. The combined organic phases were washed with brine, dried and evaporated. The residual oil was dissolved in dry diethyl ether (250 mL), cooled in ice and treated dropwise with a solution of ethylenediamine (47 mL, 355 mmol) in dry diethyl ether (150 mL) and stirred at room temperature for 0.5 h. The mixture was washed with 0.5 M aq. hydrochloric acid and brine and the organic phase was dried and evaporated. After trituration with diethyl ether and cooling in ice, some precipitated N,N-di-(benzyloxycarbonyl)ethylenediamine was removed by filtration and 10 was isolated as a pale oil (28.62 g, 100%) which was used in the next step without further purification; $^1$H NMR (90 MHz) δ 7.78 (d, J=7.2 Hz, 1H), 7.00-7.56 (m, 7H), 6.58-6.72 (m, 2H), 5.42 (s, 2H), 1.03 (s, 9H), 0.22 (s, 6H).

Benzyl 4-hydroxyindole-1-carboxylate (11). A solution of 10 (28.62 g, 75 mmol) in tetrahydrofuran (375 mL) containing acetic acid (4.5 g, 75 mmol) was treated at 0° C. with 1 M tetrabutylammonium fluoride (75 mL, 75 mmol) and the mixture was stirred at 0° C. for 40 min. The solvent was evaporated and the residue was dissolved in diethyl ether (250 mL) and washed with saturated aq. sodium bicarbonate and brine, dried and evaporated to give a brown solid which was washed with cold hexanes to give 11 as white fluffy needles (14.13 g, 70%), mp 118-120° C. (from dichloromethane-hexanes), (lit.[11] mp 121-124° C.).

Benzyl 4-[di(ethoxycarbonyl)methoxy]indole-1-carboxylate (12). The indole 11 (10.69 g, 40 mmol) was added to a suspension of anhydrous potassium carbonate (8.29 g, 60 mmol) in acetone (400 mL) and the mixture was stirred at room temperature for 15 min. Diethyl bromomalonate (11.47 g, 48 mmol) was added and the mixture was heated under reflux for 17 h. The solid was filtered off and washed with acetone and the combined filtrates were evaporated. The residue was dissolved in diethyl ether (150 mL), washed with 0.5 M aq. sodium hydroxide and brine, dried and evaporated to a brown viscous oil (16.87 g). After trituration with diethyl ether, the precipitated white solid was filtered off and the filtrate was evaporated. The residue was flash chromatographed [ethyl acetate-hexanes (15:85)] to give more solid and the combined solids were recrystallised to give 12 as white crystals (13.83 g, 81%), mp 77-78° C. (from ethyl acetate-hexanes); $^1$H NMR (500 MHz) δ 7.86-7.92 (br d, 1H), 7.57 (d, J=3.7 Hz, 1H), 7.47-7.49 (m, 2H), 7.36-7.43 (m, 3H), 7.20 (t, J=8.1 Hz, 1H), 6.86 (d, J=3.9 Hz, 1H), 6.63 (d, J=8.1 Hz, 1H), 5.45 (s, 2H), 5.30 (s, 1H), 4.29-4.37 (m, 4H), 1.30 (t, J=7.1 Hz, 6H). Anal. Calcd for $C_{23}H_{23}NO_7$: C, 64.93; H, 5.45; N, 3.29. Found: C, 65.06; H, 5.64; N, 3.21.

Diethyl 2-(indol-4-yloxy)malonate (8). A solution of 12 (8.51 g, 20 mmol) in ethanol (250 mL) was mixed with 10% palladium on carbon (1.5 g) and hydrogenated at atmospheric pressure for 1 h until hydrogen uptake ceased. The catalyst was filtered off through a Celite bed and washed with ethanol, and the filtrate was evaporated to give a brown oil. Filtration through flash silica with ethyl acetate-hexanes (3:2) as eluent, followed by trituration with diethyl ether-hexanes at −20° C. gave 8 as white crystals (4.78 g, 82%), mp 52-53° C. (from diethyl ether-hexanes), identical to the material described above.

4-[1,3-Bis(t-butyldimethylsilyloxy)propan-2-yloxy]indole (14). LiAlH4 (1.82 g, 48 mmol) was suspended in dry $Et_2O$ (120 mL) and cooled to 0° C. under nitrogen in a three-necked flask equipped with a reflux condenser and a pressure equalised dropping funnel. A solution of diethyl 2-(indol-4-yloxy)malonate 8 (3.50 g, 12 mmol) in dry $Et_2O$ (80 mL) was added dropwise, then the cold bath was removed and the mixture was refluxed for 2 h. The reaction mixture was then cooled to 0° C. and water (1.82 mL) was added followed by 15% aq. NaOH (1.82 mL) and finally water (3×1.82 mL). The precipitated solid was filtered off, washed thoroughly with EtOAc and the combined washings were dried and evaporated to give a viscous oil (2.63 g). This material was dissolved in dry $CH_2Cl_2$ (250 mL) and treated with imidazole (2.45 g, 36 mmol) and t-butyldimethylsilyl chloride (4.52 g, 30 mmol) and the mixture was stirred at room temperature under nitrogen overnight. The precipitated white solid was filtered off, washed with $CH_2Cl_2$ and the filtrate was washed successively with 0.5 M aq. HCl, 0.5 M aq. NaOH and brine, dried and evaporated to give 14 (4.13 g, 79%) as a colourless viscous oil: $^1$H NMR (500 MHz) δ 8.11 (br s, 1H), 6.99-7.12 (m, 3H), 6.61-6.67 (m, 2H), 4.51 (quintet, J=5 Hz, 1H), 3.86-3.95 (m, 4H), 0.89 (s, 18H), 0.07 (s, 6H), 0.03 (s, 6H). HRMS (ES$^+$): m/z 436.2718 (M+H)$^+$; calcd for $(C_{23}H_{41}NO_3Si_2+H)^+$, 436.2698.

1-[4-(N-Phthalimido)butanoyl]-4-[1,3-bis(t-butyldimethylsilyloxy)propan-2-yloxy]indoline (15) and related compounds. $NaBH_3CN$ (1.79 g, 28.5 mmol) was added portionwise to a solution of the indole 14 (4.13 g, 9.5 mmol) in acetic acid (90 mL) and the mixture was stirred at room temperature for 1 h. The solvent was evaporated and the residue was diluted with water, neutralised with solid $NaHCO_3$ and extracted with EtOAc. The combined organic phases were washed with brine, dried and evaporated to give 4-[1,3-bis(t-butyldimethylsilyloxy)propan-2-yloxy]indoline (3.14 g, 75%) as a viscous oil: $^1$H NMR (90 MHz) δ 6.82 (t, J=7.2 Hz 1H), 6.04-6.32 (m, 2H), 4.16-4.32 (m, 1H), 3.64-3.88 (m, 4H), 3.46 (t, J=7.2 Hz, 2H), 2.88 (t, J=7.2 Hz, 2H), 2.04 (s, 1H), 0.88 (s, 18H), 0.04 (s, 12H). This material was dissolved in dry MeCN (95 mL) and treated with 4-(N-phthalimido) butanoic acid (2.66 g, 11.4 mmol) and 1-(3-dimethylaminopropyl)-3-ethylcarbodiimide hydrochloride (2.55 g, 13.3 mmol) and the mixture was stirred at room temperature overnight. The solvent was evaporated and the residue was taken up in EtOAc, washed with 0.5 M aq. HCl, aq. $NaHCO_3$ and brine, dried and evaporated. Flash chromatography [EtOAc-hexanes (1:4)→(2:3)→(1:1)] gave four products. The first eluted material was 15 (1.69 g) as white crystals, mp 118-120° C. (MeOH). This material was estimated by $^1$H NMR to contain ~20% of 1-[4-(N-phthalimido)butanoyl]-4-[1-(t-butyldimethylsilyloxy)propan-2-yloxy]indoline 16. The second eluted material was 1-[4-(N-phthalimido)butanoyl]-4-[1-(t-butyldimethylsilyloxy)propan-2-yloxy]indoline 16 (0.22 g, 6%) as white crystals, mp 118-120° C. ($Et_2O$-hexanes): $^1$H NMR (500 MHz) δ 7.81 (dd, J=5.4, 2.9 Hz, 2H), 7.71 (d, J=8.2 Hz, 1H), 7.68 (dd, J=5.4, 2.9 Hz, 2H), 7.07 (t, J=8.2 Hz, 1H), 6.51 (d, J=8.2 Hz, 1H), 4.13-4.19 (m, 1H), 4.02 (t, J=8.5 Hz, 2H), 3.74-3.92 (m, 6H), 3.10 (t, J=8.5 Hz, 2H), 2.47 (t, J=7.1 Hz, 2H), 2.15 (quintet, J=7.1 Hz, 2H), 1.23 (d, J=6.2 Hz, 3H), 0.90 (s, 9H), 0.10 (s, 3H), 0.08 (s, 3H). LRMS (ES$^+$); calcd for $(C_{29}H_{38}N_2O_5Si+H)^+$, 523; found, 523.4. Anal. Calcd for $C_{29}H_{38}N_2O_5Si+H_2O$: C, 64.64; H, 7.45; N, 5.18. Found: C, 64.70; H, 7.13; N, 5.12.

The third eluted material was 1-[4-(N-phthalimido)butanoyl]-4-[1-(acetoxy)-3-(t-butyldimethylsilyloxy)propan-2-yloxy]indoline 17 (0.15 g, 4%) as colourless viscous oil: $^1$H NMR (500 MHz) δ 7.81 (dd, J=5.4, 2.9 Hz, 2H), 7.67-7.74 (m, 3H), 7.07 (t, J=8.2 Hz, 1H), 6.63 (d, J=8.2 Hz, 1H), 4.52 (quintet, J=5.2 Hz 1H), 4.28-4.36 (m, 2H), 4.01 (t, J=8.5 Hz, 2H), 3.77-3.85 (m, 4H), 3.08 (t, J=8.5 Hz, 2H), 2.47 (t, J=7.1 Hz, 2H), 2.15 (quintet, J=7.1 Hz, 2H), 2.04 (s, 3H), 0.90 (s, 9H), 0.05 (s, 3H), 0.04 (s, 3H). LRMS (ES$^+$) m/z: calcd for $(C_{31}H_{40}N_2O_7Si+H)^+$, 581; found, 581.3.

The fourth eluted material was 1-[4-(N-phthalimido)butanoyl]-4-[1-(t-butyldimethylsilyloxy)-3-(hydroxy)propan-2-yloxy]indoline 18 (0.48 g, 13%) as white crystals, mp 74-76° C. (from EtOAc-hexanes): $^1$H NMR (500 MHz) δ 7.82 (dd, J=5.4, 2.9 Hz, 2H), 7.73 (d, J=8.2 Hz, 1H), 7.68 (dd, J=5.4, 2.9 Hz, 2H), 7.07 (t, J=8.2 Hz, 1H), 6.62 (d, J=8.2 Hz, 1H), 4.41 (quintet, J=5 Hz, 1H), 4.03 (t, J=8.5 Hz, 2H), 3.80-3.95 (m, 6H), 3.10 (t, J=8.5 Hz, 2H), 2.48 (t, J=7.1 Hz, 2H), 2.10-19 (m, 3H), 0.90 (s, 9H), 0.07 (s, 3H), 0.06 (s, 3H). Anal. Calcd for $C_{29}H_{38}N_2O_6Si$: C, 64.66; H, 7.11; N, 5.20. Found: C, 64.44; H, 7.10; N, 5.06.

1-[4-(N-Phthalimido)butanoyl]-4-[(1,3-dihydroxy)propan-2-yloxy]indoline (19). The indole 14 (3.88 g, 8.9 mmol) was reduced and coupled with 4-(N-phthalimido)butyric acid as described above. The crude product (5.84 g) was dissolved in THF and treated with acetic acid (1.18 g, 18.2 mmol) and TBAF (1 M solution in THF; 16.6 mL, 16.6 mmol) and the mixture was kept at room temperature for 24 h. The solvent was concentrated to ~50 mL, diluted with EtOAc (350 mL) and washed with brine (2×400 mL). The organic phase was allowed to stand and the white precipitate formed was filtered off, washed with cold EtOAc and dried under vacuum. The filtrate was washed with saturated aq. $NaHCO_3$ and brine, dried and evaporated to give more solid. The combined solids were recrystallised from MeOH to give 19 (1.99 g, 57%) as white crystals, mp 173-175° C.: $^1$H NMR ($CDCl_3$-DMSO-$d_6$, 500 MHz) δ 7.80 (dd, J=5.4, 2.9 Hz, 2H), 7.72 (dd, J=5.4, 2.9 Hz, 2H), 7.65 (d, J=8.2 Hz, 1H), 7.03 (t, J=8.2 Hz, 1H), 6.69 (d, J=8.2 Hz, 1H), 4.36 (quintet, J=5.1 Hz, 1H), 4.16 (t, J=6.1 Hz, 2H), 4.03 (t, J=8.5 Hz, 2H), 3.77-3.82 (m, 6H), 3.14 (t, J=8.5 Hz, 2H), 2.48 (t, J=7.0 Hz, 2H), 2.10 (quintet, J=7.0 Hz, 2H); HRMS (MALDI): calcd for $(C_{23}H_{24}N_2O_6+H)^+$, 425.1707; found, 425.1695. Anal. Calcd for $C_{23}H_{24}N_2O_6$: C, 65.08; H, 5.70; N, 6.60. Found: C, 64.84; H, 5.68; N, 6.59.

1-[4-(N-Phthalimido)butanoyl]-4-{(1,3-bis[di(t-butoxy) phosphoryloxy]-propan-2-yloxy}indoline (20). A suspension of the diol 19 (0.98 g, 2.3 mmol) in dry THF (115 mL) was treated under nitrogen with 1H-tetrazole (1.29 g, 18.4 mmol) and di-t-butyl-N,N-diethylphosphoramidite (93% purity; 2.47 g, 9.2 mmol) and the mixture was stirred under nitrogen at room temperature overnight. The solution was cooled to 0° C. and treated dropwise with a solution of m-chloroperbenzoic acid (55% peracid; 4.33 g, 13.8 mmol) in $CH_2Cl_2$ (115 mL). The solution was stirred at 4° C. for 1 h, diluted with $CH_2Cl_2$ and washed successively with 10% aq. $Na_2S_2O_5$, saturated aq. $NaHCO_3$ and brine, dried and evaporated. Flash chromatography [MeOH-EtOAc (2:98)] gave 20 (1.79 g, 96%) as a white foam: $^1$H NMR (500 MHz) δ 7.81 (dd, J=5.3, 2.1 Hz, 2H), 7.73 (d, J=8.2 Hz, 1H), 7.69 (dd, J=5.3, 3.1 Hz, 2H), 7.08 (t, J=8.2 Hz, 1H), 6.67 (d, J=8.2 Hz, 1H), 4.67 (quintet, J=4.9 Hz, 1H), 4.17 (dd, J=6.6, 5.1 Hz, 4H), 4.00 (t, J=8.4 Hz, 2H), 3.82 (t, J=6.5 Hz, 2H), 3.11 (t, J=8.4 Hz, 2H), 2.47 (t, J=7.1 Hz, 2H), 2.14 (quintet, J=6.8 Hz, 2H), 1.47 (s, 18H), 1.46 (s, 18H). HRMS (ES$^+$): calcd for $(C_{39}H_{58}N_2O_{12}P_2+H)^+$, 809.3538; found, 809.3519.

1-(4-Aminobutanoyl)-4-[1,3-bis(dihydroxyphosphoryloxy)propan-2-yloxy]-7-nitroindoline (6). To a solution of 20 (437 mg, 0.54 mmol) in a mixture of dry $CH_2Cl_2$ (10 mL) and acetic anhydride (20 mL) was added copper nitrate hemipentahydrate (137 mg, 0.59 mmol) and the mixture was stirred at room temperature overnight, then filtered and concentrated in vacuo. The residue was re-evaporated from toluene (2×20 mL), diluted with EtOAc (50 mL) and washed with saturated aq. $NaHCO_3$ (2×50 mL) and brine, dried and evaporated to a brown viscous oil (254 mg). Flash chromatography [EtOAc-MeOH (96:4)] gave a pale viscous oil (105 mg), and this step was omitted in later runs. This material was dissolved in TFA (10 mL), stirred at room temperature for 1 h and concentrated in vacuo. The residue was dissolved in cold, 250 mM Na phosphate pH 6.0 (24 mL) and adjusted carefully to pH 6.0 with 1 M aq. NaOH. The solution was washed with ether and analysed by reverse-phase HPLC [mobile phase 25 mM Na phosphate, pH 6.0-MeCN (100:12.5 v/v)]. There was a major and a minor peak, with $t_R$ 19.8 and 24.8 min respectively, that were later identified as 7- and 5-nitro isomers. The solution was diluted to 50 mL with 25 mM Na phosphate, pH 6.0 and pumped onto the preparative HPLC column, that was previously equilibrated with 25 mM Na phosphate, pH 6.0. The column was first washed with the same buffer for 3 h, then eluted with 25 mM Na phosphate, pH 6.0-MeCN (10:1 v/v). Fractions containing the main peak were analysed by reverse-phase HPLC as above, combined and quantified by UV spectroscopy at 340 nm (46 μmol), and concentrated. The residue was dissolved in water (20 mL) and desalted by re-application to the preparative HPLC column, which was again pre-equilibrated in 25 mM Na phosphate, pH 6.0. The column was first washed with this buffer for 1 h and then with water. The product began to elute in the water wash and elution was completed with water-MeCN (100:15 v/v). Fractions were analysed as above, combined and quantified by UV spectroscopy (41 μmol). The solution was concentrated and the residue taken up in water (9 mL) and lyophilised. The yellow powder was dissolved in water (2 mL) and exchanged its tetrakis(tetrabutyl) ammonium salt by application to a 1×20 cm column of Dowex 50 ($Bu_4N^+$ form). The eluate was lyophilised and re-dissolved in water (1 mL). The solution was diluted with isopropanol (4 mL) and treated with $NaBH_4$ (15 mg, 0.4 mmol) in two portions over a period of 1 h and the mixture was stirred at room temperature overnight. The solution was then acidified to pH 4-5 with glacial acetic acid, heated to 80° C. for 3.5 h and the solvent was evaporated. The residue was dissolved in water (20 mL) and adjusted to pH 6.0 with 1 M aq. NaOH, then washed with ether and analysed by both reverse-phase HPLC (mobile phase 100 mM Na phosphate, pH 6.0, ($t_R$ 5.2 min, large peak and 8.8 min, small peak) and anion exchange HPLC (mobile phase 100 mM Na phosphate, pH 6.0-MeCN (5:1, v/v), ($t_R$ 5.2 min, large peak and 9.4 min, small peak). The eluent corresponding to the smaller peak in both analytical columns was collected separately and its UV spectrum in each case suggested that the product was the salt of 4-[1,3-bis(dihydroxyphosphoryloxy)propan-2-yloxy]-7-nitroindoline 23. The main solution was diluted with water to a conductivity of 0.85 mS $cm^{-1}$ and subjected to anion-exchange chromatography on DEAE-cellulose (column 2×20 cm) using a linear gradient formed from 10 and 500 mM NaOAc, pH 6.0 (each 250 mL). Fractions containing the product, which eluted at ~260 mM NaOAc, were analysed as above, combined and quantified by UV spectroscopy (10 μmol). The solution was concentrated and the residue was taken up in water (5 mL), passed through a 0.2 μm membrane, treated with 2 M $Ba(OAc)_2$ (1 mL) and EtOH (2.5 mL) and allowed to stand at 4° C. overnight. The mixture was centrifuged and the supernatant, re-quantified by UV spectroscopy, showed that ~80% of the compound had precipitated as its barium salt. The precipitate was washed water-EtOH (1:1) (3×8 mL) and redissolved in water (3 mL) and mixed with Dowex 50 ($Na^+$ form; 0.5 g) for 1 h. The Dowex was filtered, washed with water (3 mL) and the combined filtrates were passed through a 0.2 μm membrane filter and lyophilised. The residue was dissolved in water (0.5 mL) and quantified by UV spectroscopy to give 6 (7.2 mM, 3.6 μmol) as the $Na^+$ salt. $^1$H NMR (500 MHz, $D_2O$, acetone ref.) δ 7.72 (d, J=9.2 Hz, 1H), 7.19 (d, J=9.2 Hz, 1H), 4.87 (quintet, J=4.8 Hz, 1H), 4.31 (t, J=7.8 Hz, 2H), 3.96-4.05 (m, 4H), 3.23 (t, J=7.8 Hz, 2H), 3.05 (t, J=7.7 Hz, 2H), 2.72 (t, J=7.1 Hz, 2H), 2.00 (quintet, J=7.5 Hz, 2H). LRMS (ESI) (m/z): $(M+2H)^-$ found: 498.2; calcd for $(C_{15}H_{20}N_3O_{12}P_2+2H)^-$, 498.1.

4-(1,3-Diacetoxypropan-2-yloxy)indole (24). $LiAlH_4$ (1.82 g, 48 mmol) was suspended in dry $Et_2O$ (120 mL) in a three-necked flask equipped with a reflux condenser and a pressure-equalising funnel, and the mixture was cooled to 0° C. under nitrogen. A solution of diethyl 2-(indol-4-yloxy) malonate 8 (3.49 g, 12 mmol) in dry $Et_2O$ (60 mL) was added dropwise. The cold bath was removed and the mixture was refluxed for 2 h, then cooled to 0° C. and water (1.82 mL) was added slowly, followed by 15% aq. NaOH (1.82 mL) and finally water (5.46 mL). The precipitated solid was filtered off, washed thoroughly with EtOAc and the combined filtrates were dried and evaporated to give crude 13 as a viscous oil (2.11 g). This material was dissolved in dry pyridine (25 mL), mixed with acetic anhydride (4.90 g, 48 mmol) and stirred at room temperature overnight. The solvent was evaporated and the residue was dissolved in EtOAc and washed successively with 1 M aq HCl, saturated aq. $NaHCO_3$ and brine, dried and evaporated to a viscous oil. Trituration with ether gave 24 (2.79 g, 80%) as white crystals, mp 80-81° C. (EtOAc-hexanes): $^1$H NMR (500 MHz) δ 8.21 (br s, 1H), 7.12 (dd, J=3.1, 2.4 Hz, 1H), 7.06-7.11 (m, 2H), 6.66 (dd, J=7.1, 1.1 Hz, 1H), 6.63-6.69 (m, 1H), 4.83 (quintet, J=5.3 Hz, 1H), 4.44 (dd, J=11.8, 5.6 Hz, 2H), 4.37 (dd, J=11.8, 5.0 Hz, 2H), 2.07 (s, 6H). Anal. Calcd for $C_{15}H_{17}NO_5$: C, 61.85; H, 5.88; N, 4.81. Found: C, 61.96; H, 5.98; N, 4.73.

1-(4-Azidobutanoyl)-4-(1,3-diacetoxypropan-2-yloxy)indoline (25). $NaBH_3CN$ (0.94 g, 15 mmol) was added portionwise to a solution of 24 (1.46 g, 5 mmol) in acetic acid (40 mL) and the mixture was stirred at room temperature for 1 h. The solvent was evaporated and the residue was diluted with water, neutralised with $NaHCO_3$ and extracted with EtOAc. The combined organic phases were washed with brine, dried and evaporated to give crude 4-(1,3-diacetoxypropan-2-yloxy)indoline (1.47 g, 100%) as a viscous oil: $^1$H NMR (90 MHz) δ 6.95 (t, J=7.2 Hz 1H), 6.24-6.68 (m, 2H), 4.62 (quintet, J=5.4 Hz, 1H), 4.20-4.46 (m, 4H), 3.64 (s, 1H), 4.52 (t, J=7.2 Hz, 2H), 2.94 (t, J=7.2 Hz, 2H), 2.06 (s, 6H). Without further purification, this material was dissolved in dry MeCN (40 mL) and treated with 4-azidobutyric acid (0.78 g, 6 mmol), followed by 1-(3-dimethylaminopropyl)-3-ethylcarbodiimide hydrochloride (1.34 g, 7 mmol) and the mixture was stirred at room temperature overnight. The solvent was evaporated and the residue was taken up in EtOAc (50 mL) washed with dilute aq. HCl, saturated aq. $NaHCO_3$ and brine, dried and evaporated. Flash chromatography [EtOAc-hexanes (2:3)] gave 25 (1.33 g, 64%) as white crystals, mp 61-63° C. ($Et_2O$-hexanes); $^1$H NMR (500 MHz) δ 7.87 (d, J=8.2 Hz, 1H), 7.16 (t, J=8.2 Hz, 1H), 6.68 (d, J=8.2 Hz, 1H), 4.70 (quintet, J=5.3 Hz, 1H), 4.34 (dd, J=11.9, 5.7 Hz, 2H), 4.29 (dd, J=11.9, 4.8 Hz, 2H), 4.07 (t, J=8.5 Hz, 2H), 3.45 (t, J=6.4 Hz, 2H), 3.12 (t, J=8.4 Hz, 2H), 2.51 (t, J=6.9 Hz, 2H), 2.06 (s, 6H), 2.03 (quintet, J=6.6 Hz, 2H). Anal. Calcd for $C_{19}H_{24}N_4O_6$: C, 56.43; H, 5.98; N, 13.85. Found: C, 56.23; H, 5.98; N, 13.61.

1-(4-Azidobutanoyl)-4-(1,3-diacetoxypropan-2-yloxy)-7-nitroindoline (26). A solution of 25 (1.02 g, 2.5 mmol) in a mixture of $CH_2Cl_2$ (25 mL) and acetic anhydride (50 mL) was treated with copper nitrate hemipentahydrate (0.64 g, 2.75 mmol) and stirred at room temperature. The reaction progress was monitored by TLC [EtOAc-hexanes (1:1)] and after 25 h the solution was concentrated. The residue was re-evaporated from toluene, diluted with EtOAc (50 mL) and washed with saturated aqueous $NaHCO_3$ and brine, dried and evaporated to give a brown viscous oil. Flash chromatography [EtOAc-hexanes (1:1)] gave a solid (0.96 g) that was recrystallised (EtOAc-hexanes) to give 26 (0.78 g, 70%) as yellow crystals, mp 101-102° C.; $\lambda_{max}$ (EtOH)/nm (ε/$M^{-1}cm^{-1}$) 249 (22 280), 299 (5270); $\lambda_{max}$ [EtOH-25 mM Na phosphate, pH 7.0 (1:24)]/nm ($\epsilon$/M$^{-1}$cm$^{-1}$) 247 (19 750), 330 (4800); $^1$H NMR (500 MHz) δ 7.74 (d, J=9.1 Hz, 1H), 6.79 (d, J=9.1 Hz, 1H), 4.80 (quintet, J=5.3 Hz, 1H), 4.35 (dd, J=12.0, 5.8 Hz, 2H), 4.30 (dd, J=12.0, 4.7 Hz, 2H), 4.24 (t, J=8.1 Hz, 2H), 3.44 (t, J=6.4 Hz, 2H), 3.10 (t, J=8.1 Hz, 2H), 2.58 (t, J=6.8 Hz, 2H), 2.07 (s, 6H), 2.02 (quintet, J=6.4 Hz, 2H). Anal. Calcd for $C_{19}H_{23}N_5O_8$: C, 50.78; H, 5.16; N, 15.58. Found: C, 50.86; H, 5.21; N, 15.64.

1-(4-Azidobutanoyl)-4-(1,3-dihydroxypropan-2-yloxy)-7-nitroindoline (27). A solution of 26 (0.76 g, 1.7 mmol) in MeOH (85 mL), water (8.5 mL) and 1 M aq. NaOH (4.1 mL, 4.1 mmol) was stirred at room temperature for 2 min, quenched with 1 M citric acid (8.5 mL) and concentrated under reduced pressure to ~20 mL. The solution was diluted with water (30 mL), washed with EtOAc (3×50 mL) and the combined organic washings were washed with saturated aq. NaHCO$_3$ and brine, dried and evaporated to a brown viscous oil which after trituration with Et$_2$O gave 27 (0.49 g, 78%) as yellow needles, mp 78-79° C. (EtOAc-hexanes); $^1$H NMR (500 MHz) δ 7.70 (d, J=9.2 Hz, 1H), 6.76 (d, J=9.2 Hz, 1H), 4.57 (quintet, J=4.8 Hz, 1H), 4.25 (d, J=8.1 Hz, 2H), 3.95 (dd, J=11.9, 4.8 Hz, 2H), 3.92 (dd, J=11.9, 4.8 Hz, 2H), 3.43 (t, J=6.4 Hz, 2H), 3.14 (t, J=8.0 Hz, 2H), 2.57 (t, J=6.9 Hz, 2H), 2.03 (t, J=7.6 Hz, 2H), 2.02 (quintet, J=6.4 Hz, 2H); HRMS (ESI) (m/z): Calcd for $(C_{15}H_{19}N_5O_6+H)^+$, 366.1408. Found: 366.1427.

1-(4-Azidobutanoyl)-4-[1,3-bis(dihydroxyphosphoryloxy)propan-2-yloxy]-7-nitroindoline (28). Pyrophosphoryl chloride (1.81 g, 7.2 mmol) was added at 0° C. to a suspension of the diol 27 (146 mg, 0.4 mmol) in anhydrous EtOAc (8.8 mL), and the mixture was stirred at 0° C. for 3 h. The reaction was quenched by the addition of ice-cold water (60 mL), adjusted to pH 6.6 with cold 1 M triethylammonium bicarbonate (TEAB), pH 7.8 (60 mL) and washed with Et$_2$O (3×50 mL). The aqueous phase was concentrated under reduced pressure to ~50 mL and the pH was adjusted to 7.0 by careful addition of Et$_3$N. The neutral solution (50 mL) was passed through a 0.2 μm membrane filter and analysed by anion-exchange HPLC (mobile phase 100 mM Na phosphate, pH 6.0-MeCN (5:1 v/v), $t_R$ 5.2 min) and also by reverse-phase HPLC (mobile phase 25 mM Na phosphate, pH 6.0-MeCN (25:1 v/v), $t_R$ 14.2 min). The solution was then loaded onto the preparative reverse-phase HPLC column (equilibrated with 25 mM triethylammonium phosphate, pH 6.0), that was first washed with the same equilibration buffer for 2 h, then with water. The product eluted after ~45 min when the conductivity of the eluate reduced to that of water. Fractions containing the product were analysed by anion-exchange HPLC as above, combined and quantified by UV spectroscopy based on $\epsilon_{330}$ 4800 M$^{-1}$cm$^{-1}$ (198 μmol). The solution was concentrated to ~15 mL, passed through a 0.2 μm membrane filter and lyophilised to a pale yellow solid. The solid was dissolved in water (2 mL) and an aliquot (50 μL, 5 μmol) was exchanged to the Na$^+$ salt (Dowex 50). $^1$H NMR (500 MHz, D$_2$O, acetone ref.) δ 7.82 (d, J=9.0 Hz, 1H), 7.12 (d, J=9.3 Hz, 1H), 4.90 (quintet, J=5.5 Hz, 1H), 4.35 (t, J=7.8 Hz, 2H), 4.07-4.16 (m, 4H), 3.43 (t, J=6.8 Hz, 2H), 3.22 (t, J=7.9 Hz, 2H), 2.72 (t, J=6.2 Hz, 2H), 1.96 (quintet, J=6.4 Hz, 2H).

1-(4-Aminobutanoyl)-4-[1,3-bis(dihydroxyphosphoryloxy)propan-2-yloxy]-7-nitroindoline (6). A solution of 27 (193 μmol) in water (2 mL) was diluted with DMF (18 mL) and treated with triphenylphosphine (355 mg, 1.35 mmol), and the mixture was stirred under nitrogen at room temperature for 20 h. The solution was concentrated under reduced pressure and the residue was diluted with water (60 mL). The suspension (pH 3.1) was washed with EtOAc (3×50 mL) and the aqueous phase was separated. Reverse-phase HPLC analysis (mobile phase 25 mM Na phosphate, pH 6.0-MeCN (25:1 v/v) confirmed that all the azide was reduced, and the solution was adjusted to pH 1.0 with 1 M aq. HCl and stirred at room temperature overnight. Analysis by anion-exchange HPLC [mobile phase 100 mM Na phosphate, pH 6.0-MeCN (5:1 v/v)] confirmed complete hydrolysis of the intermediate product 29 (see below). The solution was neutralised to pH 6.0 with 1 M aq. NaOH, diluted with water to conductivity 2.6 mS cm$^{-1}$ and subjected to anion-exchange chromatography on DEAE-cellulose as described in the preparation of 6 above, using a linear gradient formed from 10 and 550 mM NaOAc, pH 6.0 (each 1000 mL). Fractions containing the product, which eluted at ~300 mM NaOAc, were analysed as above, combined and quantified by UV spectroscopy (152 μmol). The solution was concentrated to ~10 mL, diluted with water to 16 mL, treated with 2 M Ba(OAc)$_2$ (4 mL) and EtOH (8 mL) and allowed to stand at 4° C. overnight. The mixture was centrifuged and the supernatant was analysed by UV spectroscopy, which showed 90% precipitation of the original content of 6. The precipitate was washed with water-EtOH (1:1) (5×20 mL), by vigorous shaking and centrifugation of the suspension after each wash. The final precipitate was dissolved in water (30 mL) and mixed with Dowex 50 (Na$^+$ form; 5 g) for 2 h. The resin was filtered off, washed with water (20 mL) and the combined filtrate and washings were adjusted to pH 7.0 with 1 M aq. HCl. The filtrate was passed through a 0.2 μm membrane filter and lyophilised, and the residue was dissolved in water (4 mL) and quantified by UV spectroscopy to give pure 6 (33.15 mM, 133 μmol) as the Na$^+$ salt; identical to that characterised above by $^1$H NMR spectrometry.

In an earlier experiment, the intermediate product 29 1-{4-[(N-triphenylphosphoranylidene)amino]butanoyl}-4-[1,3-bis(dihydroxyphosphoryloxy)propan-2-yloxy]-7-nitroindoline was isolated and characterised as follows. This enabled secure identification of products formed in the triphenylphosphine reduction of 28 and subsequent hydrolysis of 29.

The sample of 29 was isolated from a reaction mixture similar to that above by preparative reverse-phase HPLC, and was eluted from the column with water-MeCN (5:1 v/v). The product in analytical anion-exchange HPLC [mobile phase 100 mM Na phosphate, pH 6-MeCN (5:1 v/v)] had $t_R$ 5.4 min (compared to $t_R$ 3.8 min for 6 in the same system). $^1$H NMR (500 MHz, D$_2$O, acetone ref.) δ 7.67-7.80 (m, 10H), 7.62-7.66 (m, 6H), 7.12 (d, J=8.6 Hz, 1H), 4.90 (quintet, J=4.8 Hz, 1H), 4.08-4.14 (m, 4H), 4.04 (t, J=8.0 Hz, 2H), 3.19 (dt, J=7.1, 6.1 Hz, 2H), 3.10 (t, J=7.9 Hz, 2H), 2.53 (t, J=6.6 Hz, 2H), 1.89 (quintet, J=6.8 Hz, 2H). LRMS (ESI) (m/z): Calcd for $(C_{33}H_{32}N_3O_{12}P_3+3H)^-$, 758.1; Found: 758.1.

REFERENCES

The following references are all expressly incorporated by reference.

1. G. Papageorgiou, D. C. Ogden, A. Barth and J. E. T. Corrie. *J. Am. Chem. Soc.* 121, 6503-6504, 1999.
2. (a) G. Papageorgiou and J. E. T. Corrie. *Tetrahedron* 56, 8197-8205, 2000; (b) G. Papageorgiou and J. E. T. Corrie. *Synth. Commun.* 32, 1571-1577, 2002.
3. J. Morrison, P. Wan, J. E. T. Corrie and G. Papageorgiou. *Photochem. Photobiol. Sci.* 1, 960-969, 2002.
4. M. Canepari, L. Nelson, G. Papageorgiou, J. E. T. Corrie and D. Ogden. *J. Neurosci. Methods* 112, 29-42, 2001.
5. (a) M. Canepari, G. Papageorgiou, J. E. T. Corrie, C. Watkins and D. Ogden. *J. Physiol.* 533, 765-772, 2001; (b) M. Canepari, L. Nelson, G. Papageorgiou, J. E. T. Corrie and D. Ogden. *J. Neurosci. Methods* 112, 29-42, 2001; (c) M. Matsuzaki, G. C. R. Ellis-Davies, T. Nemoto, Y. Miyashita, M. Iino and M. Kasai, *Nat. Neurosci.*, 4, 1086-1092, 2001; (d) M. Canepari and D. Ogden. *J. Neurosci.* 23, 4066-4071, 2003; (e) G. Lowe. *J. Neurophysiol.* 90, 1737-1746, 2003; (f) G. M. G. Shepherd, T. A. Pologruto and K. Svoboda. *Neuron*, 38, 277-289, 2003; (g) M. A. Smith, G. C. R. Ellis-Davies and J. C. Magee. *J. Physiol.*, 548, 245-258, 2003; (h) M. Matsuzaki, N. Honkura, G. C. R. Ellis-Davies and H. Kasai. *Nature*, 429, 761-766, 2004; (i) A. G. Carter and B. L. Sabatini. *Neuron*, 44, 483-493, 2004; (j) I. Bureau, G. M. G. Shepherd and K. Svoboda. *Neuron*, 42, 789-801, 2004; (k) M. Canepari, C, Auger and D. Ogden. *J. Neurosci.*, 24, 3563-3573, 2004; (m) Y. H. H. Huang, S R. Sinha, O. D. Fedoryak, G. C. R. Ellis-Davies and D. E. Bergles. *Biochemistry*, 44, 3316-3326, 2005; (n) W. Maier, J. E. T. Corrie, G. Papageorgiou, B. Laube and C. Grewer. *J. Neurosci. Methods* 142, 1-9, 2005.
6. K. R. Gee, R. Wieboldt and G. P. Hess. *J. Org. Chem.* 116, 8366-8367.
7. Murov, S. L. *Handbook of Photochemistry*, Marcel Dekker, New York, 1973.
8. (a) Fertig, N.; Blick, R. H.; Behrends, J. C. *Biophys. J.* 2002, 82, 3056; (b) Klemic, K. G.; Sigworth, F. J. *Biophys. J.*, 2003, 84, 135a; (c) Costantin, J. L.; Wittel, A.; Lachnit, W. *Biophys. J.*, 2003, 84, 295a; (d) Friis, S.; Krzywkowski, K. M.; Asmild, M.; Jacobsen, R. B.; Oswald, N.; Schrøeder, R. L.; Willumsen, N. J. *Biophys. J.*, 2003, 84, 295a; (e) Ng, K.; Cutler, T.; Kelly, A.; Weihe, O.; Velkovska, S.; Warfield, R.; Li, X.; Shetty, S.; Grove, R.; Yang, N. *Biophys. J.*, 2003, 84, 296a.
9. G. Papageorgiou and J. E. T. Corrie. *Synth. Commun.* 32, 1571-1577, 2002.
10. J. O. Osby, M. G. Martin and B. Ganem. *Tetrahedron Lett.* 25, 2093-2096, 1984.
11. C. Kaneko, W. Okuda, Y. Karasawa and M. Somei, *Chem. Lett.*, 547, 1980.
12. T. Curtius and W. Guilini. *Ber. Deut. Chem. Ges.*, 1912, 45, 1045-1050.
13. (a) E. J. Prisbe, J. C. Martin, D. P. C. McGee, M. F. Barker, D. F. Smee, A. E. Duke, T. R. Matthews and J. P. H. Verheyden. *J. Med. Chem.*, 1986, 29, 671-675; (b) E. N. Kalinichenko, T. L. Podkopaeva, E. V. Budko, F. Seela, B. Dong, R. Silverman, J. Vepsäläinen, P. F. Torrance and I. A. Mikhailopulo. *Bioorg. Med. Chem.* 2004, 12, 3637-3647.

The invention claimed is:

1. A compound represented by the formula:

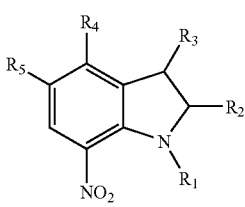

wherein:
$R_1$ is selected from the group consisting of —CO—CH$_2$—NH$_2$, —CO—CH$_2$—CH$_2$—CH$_2$—NH$_2$, —CO—CH(CH$_2$—CH$_2$—COOH)—NH$_2$ and —CO—CH$_2$—CH$_2$—CH(COOH)—NH$_2$;

$R_2$ and $R_3$ are selected from hydrogen, a substituted or unsubstituted alkyl group, or $R_2$ and $R_3$ together form a substituted or unsubstituted cycloalkyl group;

$R_4$ is a group represented by the formula:

—O—CH$_2$CH(OPO$_3^{2-}$)CH$_2$OPO$_3^{2-}$, or

—OCH(CH$_2$OPO$_3^{2-}$)$_2$, or

—O—CH$_2$(CHOPO$_3^{2-}$)$_2$CH$_2$OPO$_3^{2-}$, or

—O—CH$_2$C(CH$_2$OPO$_3^{2-}$)$_3$, or

—O(CH$_2$)$_a$OP$_2$O$_6^{3-}$, or

—O(CH$_2$)$_a$OP$_3$O$_9^{4-}$ wherein when a is present in the formula, it is an integer between 1 and 5; and $R_5$ is hydrogen, a substituted or unsubstituted alkyl group, a substituted or unsubstituted phenyl group, a triplet sensitizing group selected from the group consisting of unsubstituted and substituted benzophenones, substituted and unsubstituted anthrones, substituted and unsubstituted xanthones, substituted and unsubstituted carbazoles, substituted and unsubstituted triphenylenes and substituted and unsubstituted 3- or 4-benzoylpyridines, a group represented by (CH$_2$)$_n$Y or (CH$_2$)$_m$—O—(CH$_2$)$_n$Y;

wherein m and n are independently between 1 and 10 and Y is selected from hydrogen, CO$_2$H or salts thereof, OPO$_3^{2-}$ or salts thereof, OSO$_3^-$ or salts thereof, or CO$_2$R$_6$, wherein R$_6$ is an alkyl or substituted alkyl group;

or a salt, protected form or partially or fully protonated form of the compound.

2. A compound of the formula:

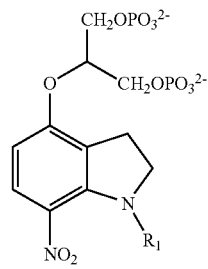

wherein:
$R_1$ represents —CO—CH$_2$—NH$_2$, —CO—CH$_2$—CH$_2$—CH$_2$—NH$_2$, —CO—CH(CH$_2$CH$_2$COOH)—NH$_2$ or —CO—CH$_2$CH$_2$CH(COOH)—NH$_2$, or a salt, protected form or partially or fully protonated form of said compound.

3. The compound of claim 1, wherein $R_1$ is —CO—CH$_2$—NH$_2$ or $R_1$ is —CO—CH$_2$—CH$_2$—CH$_2$—NH2.

4. The compound of claim 3, wherein the compound is a Li$^+$, Na$^+$, K$^+$, Rb$^+$, Cs$^+$, trialkylammonium or tetraalkylammonium salt.

5. A method of irradiating a compound of claim 1, which comprises irradiating the compound to cause it to photolyse and release an effector species wherein said effector species is selected from the group consisting of glycine, GABA and glutamate.

6. The method of claim 5, wherein the photolysis and release steps are used in a patch clamp experiment or in a method of high throughput screening.

7. The compound of claim 3, wherein said triplet sensitizing group is a 4-substituted benzophenone or a 4,4'-disubstituted benzophenone wherein said substituent is a substituted or unsubstituted alkyl or a substituted or unsubstituted alkoxy group.

8. The compound of claim 7, wherein said benzophenone substituent is a $-O-(CH_2)_n-OPO_3^{2-}$ group, wherein n is an integer between 1 and 10.

9. The method of claim 5, wherein said effector species is selected from the group consisting of glycine and GABA.

* * * * *